US00PP19611P2

(12) United States Plant Patent
Egger

(10) Patent No.: US PP19,611 P2
(45) Date of Patent: Dec. 30, 2008

(54) ***HEUCHERELLA* PLANT NAMED 'ALABAMA SUNRISE'**

(50) Latin Name: *Heucherella*
Varietal Denomination: Alabama Sunrise

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/999,758

(22) Filed: Dec. 6, 2007

(51) Int. Cl.
*A01H 5/00* (2006.01)

(52) U.S. Cl. ..... Plt./441
(58) Field of Classification Search ..... Plt./441
See application file for complete search history.

*Primary Examiner*—Kenbt L Bell
(74) *Attorney, Agent, or Firm*—Klarquist Sparkman, LLP

(57) ABSTRACT

A new and distinct *Heucherella* plant substantially as shown and described, characterized by yellow spring leaves which change to lime green and pink tones in the fall with a strong red pattern along the veins and a white overlay throughout, large, distinctive, palmately lobed leaves, large plant size, small white flowers, and excellent vigor.

2 Drawing Sheets

Botanical denomination: *Heucherella* hybrid.
Variety designation: 'Alabama Sunrise'.

The present invention relates to a new and distinct cultivar of *Heucherella* and given the cultivar name of 'Alabama Sunrise'. *Heucherella* is in the family Saxifragaceae. *Heucherella* 'Alabama Sunrise' originated from a controlled cross between *Heuchera* 'V3' (a proprietary unreleased *Heuchera* villosa hybrid), as the seed parent, and massed selected *Tiarella,* as the pollen parent. The offspring were extremely variable and interesting. This is the first selected variety.

This new *Heucherella* is distinguished by:

1. yellow spring leaves with a strong red pattern along the veins and a slight white overlay throughout,
2. base color of yellow green and lime green on the summer leaves with pink tones on the oldest leaves,
3. large, distinctive, palmately lobed leaves,
4. large plant size,
5. and excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding asexual propagations. The present invention has not been evaluated under all possible environmental conditions. The phenotype may vary with variations in environment without a change in the genotype of the plant.

BRIEF DESCRIPTION OF THE DRAWINGS

FIG. 1 shows a one year old *Heucherella* 'Alabama Sunrise' in bloom, growing in the ground in late spring in Canby, Oreg.

FIG. 2 shows a one year old *Heucherella* 'Alabama Sunrise' in a one gallon container in the shade house in the spring in Canby, Oreg.

FIG. 3 shows a one year old *Heucherella* 'Alabama Sunrise' in the ground in the garden in late early October in Canby, Oreg.

FIG. 4 shows a one and a half year old *Heucherella* 'Alabama Sunrise' growing in the ground in winter in Canby, Oreg.

DETAILED PLANT DESCRIPTION

The following is a detailed description of the new *Heucherella* cultivar based on observations of a two-year-old specimen growing in a 2 gallon container in a cool greenhouse in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Form.*—Basal rosette, herbaceous perennial.
*Hardiness.*—USDA Zone 4 to 9.
*Size.*—25 cm tall from top of the foliage to the ground and 50 cm wide.
*Habit.*—Mounding.
*Vigor.*—Excellent.
*Roots.*—Fibrous, freely branching, fine, and white in color. Roots develop easily from cuttings.

Leaf:

*Type.*—Simple.
*Arrangement.*—Rosette.
*Shape.*—Broadly ovate.
*Lobing/division.*—5 main lobes with the terminal the longest, each with secondary lobe or lobes (the depth of the lobes varies with plant maturity and leaf age; leaves become more deeply lobed with maturity).
*Venation.*—Palmate.
*Margins.*—Crenate.
*Apex.*—Mucronulate.
*Base.*—Cordate.

*Blade size.*—10 cm to 14.5 cm long and 9 cm to 13 cm wide.

*Surface texture.*—Sparsely glandular both surfaces.

*Texture.*—Thin, leathery.

*Petiole description.*—14 cm to 18 cm long and 2.5 mm wide, glandular hairs, between Greyed Purple 187A and 187B.

*Leaf color.*—Early spring — Yellow, Green Yellow 1 B to Yellow Green 150A with veins and area around veins Greyed Purple 185A slight white veiling. Early spring bottom side, Yellow Green 144D with maroon blotch Greyed Purple 185A to Greyed Red 181A. Summer, fall topside — Lime, closest to Yellow Green 145A near margins and Yellow Green 150A near veins with blotch on and around veins Greyed Purple 185A to 187A. Summer, fall bottom side — Yellow Green 148B. Winter topside — Green with white veil, Yellow Green 146A to 146C with the blotch Greyed Purple 187A, oldest leaves Greyed Red 181D with the blotch Greyed Brown 199B.

Inflorescence:

*Size.*—4 cm wide and 25 cm long.

*Type.*—Raceme.

*Number of flowers per raceme.*—about 70.

*Number of raceme.*—10.

*Peduncle.*—40 to 58 cm tall, 3 mm wide at base, Greyed Purple 183C, glandular hairs, with 1 to 3 petiolate cauline leaves (ovate, blades 1.5 to 5 cm long and 1 to 3.5 cm wide with 3 deeply cut lobes each with lateral lobes, no blotch, crenate, mucronate, cordate, Yellow Green 144A with Greyed Purple 183A on margin and petiole).

*Pedicel.*—Grows to 12 mm long, with glandular hairs, Greyed Red 182B.

*Bloom period.*—June in Canby, Oreg.

Flower bud:

*Size.*—2 mm wide and 4 mm long.

*Description.*—glandular puberulent, ovoid.

*Color.*—White 155D.

Flower:

*Type.*—Perfect.

*Shape.*—Campanulate.

*Size.*—6 mm long and 8 mm wide.

*Petal description.*—5 in number, oblanceolate, 4 mm long and 1 mm wide, tip acuminate, base attenuate, margin entire, glabrous on both sides, White 155D on both sides.

Calyx description.—5 mm long and 5 mm wide, with 5 lobes, divided ½ way to the base, campanulate, glandular hairs on outside, glabrous inside, tip obtuse, margin entire, White 155D on both sides except tips of back side which are Yellow Green 146D.

*Stamen description.*—5 in numbers, filaments 4 mm long White 155D, anthers sterile, less than 1 mm, Greyed Orange 164B.

*Pistil description.*—One central two beaked pistil, 4 mm long, White 155C.

*Fragrance.*—None.

*Lastingness.*—Each raceme blooms for about 2 weeks on the plant.

Fruit and seed: None.

Disease and pest tolerance: No known resistance to rust, a common problem with light leaf type *Heucherella.* Excellent disease tolerance to powdery mildew. All *Heucherella* are susceptible to root weevils.

COMPARISON TO SIMILAR *HEUCHERELLA*

Compared to the seed parent, *Heuchera* 'V3' (unpatented), the new variety is lobed and greener with a red purple blotch along the vein compared to no blotch.

Compared to the pollen parent, one of a *Tiarella* mass, the new variety has yellow foliage in spring and summer rather than green.

Compared to *Heucherella* 'Kimono' (U.S. Plant Pat. No. 12,154), this new variety has spring and early summer foliage that is yellow rather than green. Leaf shape and plant habit are similar.

Compared to *Heucherella* 'Sunspot' (U.S. Plant Pat. No. 14,825), this new variety has larger and more narrowly lobed leaves, a larger habit, and white rather than pink flowers.

I claim:

1. A new and distinct *Heucherella* plant as herein illustrated and described.

* * * * *

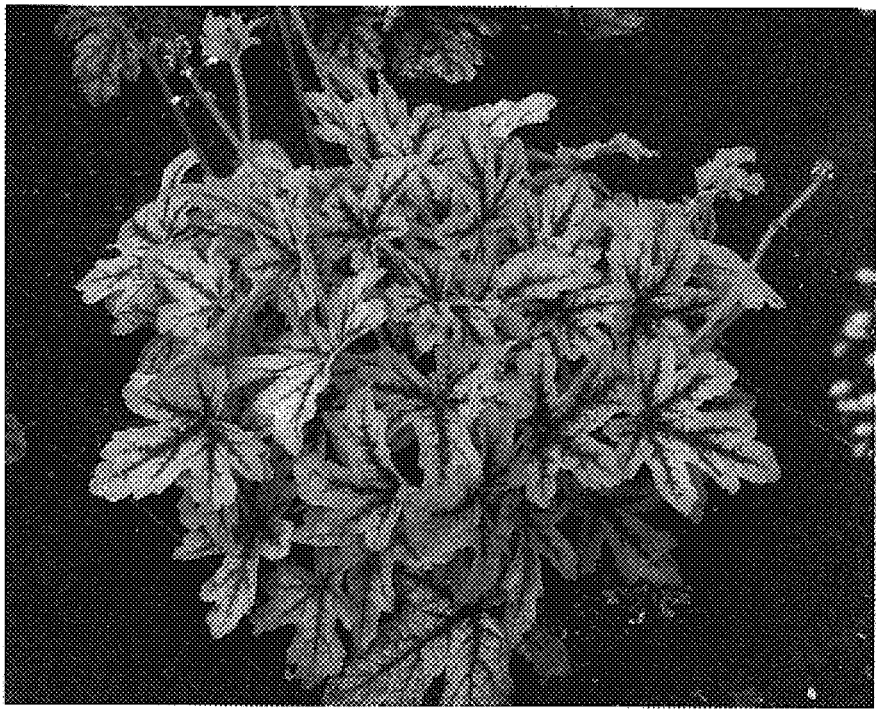
Figure 1 above. Figure 2 below.
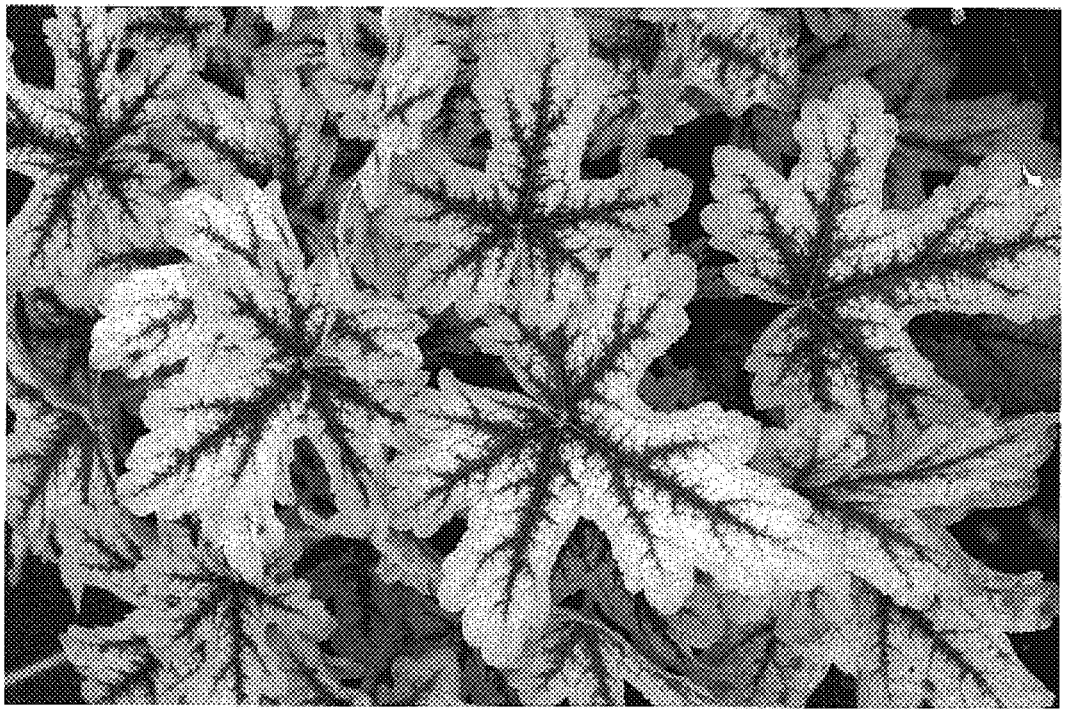

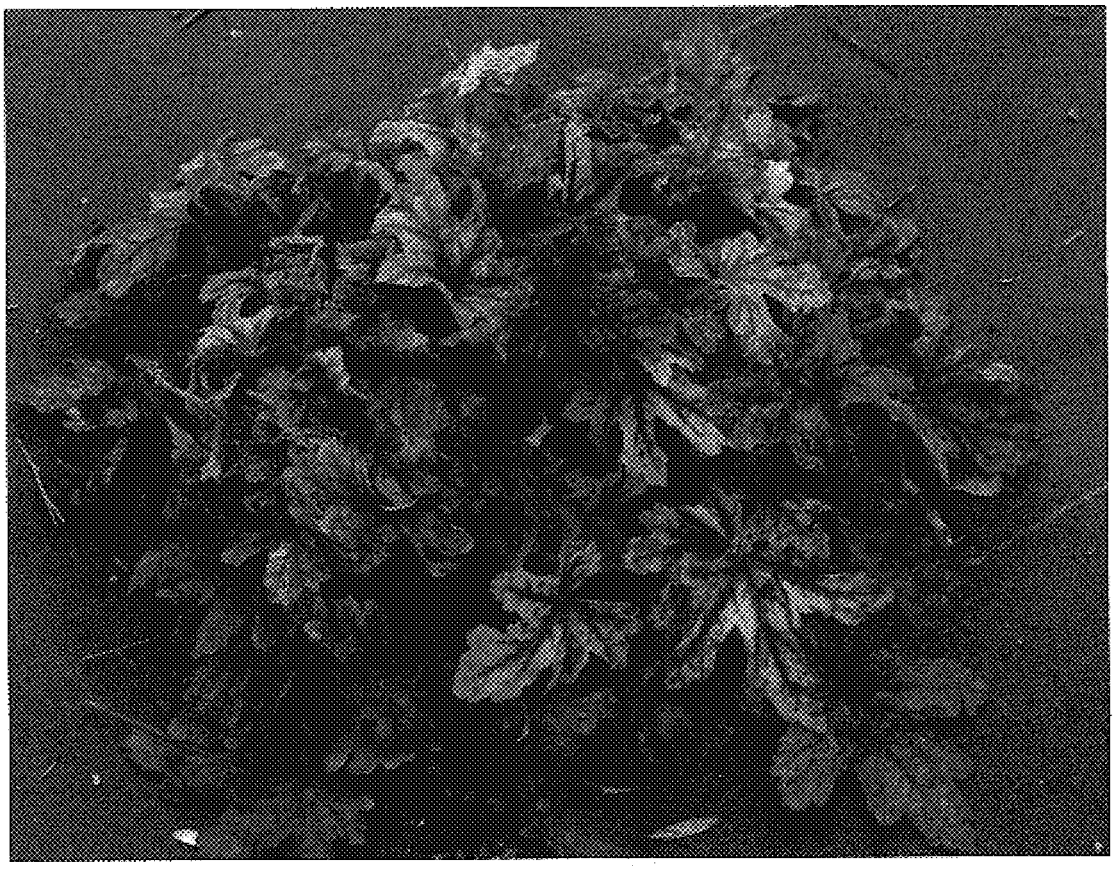

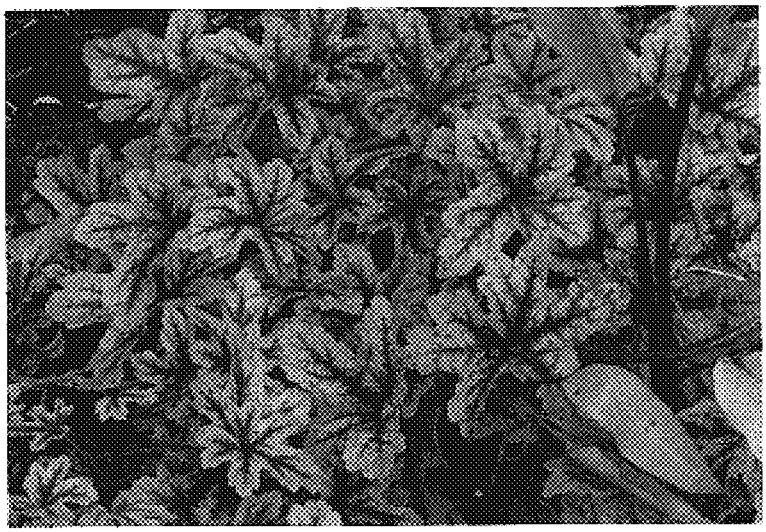
Figure 3 above. Figure 4 below.